(12) United States Patent
DeSilets et al.

(10) Patent No.: US 7,135,148 B2
(45) Date of Patent: *Nov. 14, 2006

(54) ACCESS HOLES FOR A MULTIWELL FILTER PLATE FOR MULTIWELL TEST APPARATUS

(75) Inventors: Kenneth DeSilets, Westford, MA (US); Donald Rising, Stow, MA (US); Jeanne Phillips, Littleton, MA (US)

(73) Assignee: Millipore Corporation, Billerica, MA (US)

( * ) Notice: Subject to any disclaimer, the term of this patent is extended or adjusted under 35 U.S.C. 154(b) by 508 days.

This patent is subject to a terminal disclaimer.

(21) Appl. No.: 10/166,871

(22) Filed: Jun. 11, 2002

(65) Prior Publication Data

US 2002/0192119 A1    Dec. 19, 2002

(51) Int. Cl.
*B01L 11/00* (2006.01)
(52) U.S. Cl. .................. 422/101; 422/99; 422/100; 422/102; 435/285.1; 436/180
(58) Field of Classification Search .......... 422/99–104; 435/285.1; 436/180
See application file for complete search history.

(56) References Cited

U.S. PATENT DOCUMENTS

| | | |
|---|---|---|
| 5,141,718 A | 8/1992 | Clark |
| 5,462,874 A * | 10/1995 | Wolf et al. ............ 435/297.5 |
| 5,466,602 A | 11/1995 | Lyman et al. |
| 5,650,323 A | 7/1997 | Root |
| 5,707,869 A | 1/1998 | Wolf et al. |
| 5,795,775 A | 8/1998 | Lahm et al. |
| 5,801,055 A | 9/1998 | Henderson |
| 5,837,198 A | 11/1998 | Itani |
| 5,972,694 A * | 10/1999 | Mathus ................... 435/288.4 |
| 6,309,605 B1 * | 10/2001 | Zermani .................... 422/101 |
| 6,309,608 B1 * | 10/2001 | Zhou et al. ................ 422/131 |
| 2002/0189374 A1 * | 12/2002 | DeSilets et al. ......... 73/864.51 |

FOREIGN PATENT DOCUMENTS

| | | |
|---|---|---|
| EP | 0 359 249 | 3/1990 |
| EP | 0 596 482 | 5/1994 |
| EP | 1 232 792 | 8/2002 |
| WO | WO 98/35013 | 8/1998 |
| WO | WO 99/21958 | 5/1999 |

OTHER PUBLICATIONS

International Search Report dated Jan. 21, 2003.
"Selection of Invasive and Metastatic Subpopulations from a Heterogeneous Human Melanoma Cell Line", BioTechniques, Vo. 9, No. 3 (1990), p. 324.
1. Photograph of top plate of Multi-Screen Dual Access plate prototype, publicly provided by Millipore Corporation in Feb. 1993.
2. Photograph of three piece MultiScreen Dual Access Cell Culture System prototype, publicly provided by Millipore Corporation in Feb. 1993.

* cited by examiner

*Primary Examiner*—Jill Warden
*Assistant Examiner*—Jyoti Nagpaul
(74) *Attorney, Agent, or Firm*—Millipore Corporation (57) ABSTRACT

A multiwell filter plate of a multiwell test apparatus is provided to effect addition or removal of liquid from a feeding tray positioned below the multiwell filter tray. Access holes extending through a plate of the multiwell filter plate are provided so that a syringe can be extended through the access holes.

14 Claims, 8 Drawing Sheets

ACCESS HOLES FOR A MULTIWELL FILTER PLATE FOR MULTIWELL TEST APPARATUS

BACKGROUND OF THE INVENTION

This invention relates to a multiwell filter plate for retaining a liquid and which is utilized with a multiwell test apparatus suitable for promoting fluid interactions such as by growing cells in a nutrient medium within the wells. More particularly, this invention relates to such a multiwell filter plate of a multiwell test apparatus which permits adding or removing liquid from the feeding tray of a multiwell test apparatus without disturbing a material such as cells within the wells.

At the present time, multiwell test apparatus for testing samples include a multiwell filter plate having a multiplicity of wells, a feeding tray, a multiwell receiver plate and a lid. The wells of the multiwell filter plate are formed of a tubular member with an open end to which is attached a membrane such as a microporous membrane. The tubular members can be inserted into the feeding tray containing a nutrient rich liquid medium so that cells in the wells can be attached to the membrane and grown thereon. The cells are fed as nutrients pass from the nutrient medium through the membrane and to the cells at a rate controlled by the concentration gradient of nutrients from the nutrient medium to the cells. The nutrient medium in the feeding tray is periodically replenished to maintain cell growth. It is desirable to effect replenishment of the nutrient medium quickly and in a manner which avoids damage to the membranes and the cells.

After the desired level of cell growth on the membranes of the wells has been attained, the multiwell filer plate can be utilized in conventional assay methods. These assay methods generally are effected by positioning the membranes and cells on the multiwell filter plate into the wells of the multiwell receiver plate, such as a 96 well plate positioned below the multiwell filter plate or it just has to have the same number of wells in register with the cell/filter plate. The wells of the multiwell filter plate contain a liquid composition to be assayed. The composition to be assayed diffuses into the cells and then through the membrane into the bottom receiver plate, The resultant liquid product within the wells of the multiwell filter plate or in the wells of the multiwell receiver plate then is assayed to determine the capability of the composition being assayed to permeate the cell barrier.

An important component in the drug discovery and development process is the determination of the oral absorption and bioavailability of new compounds. In order to perform this evaluation in a cost effective, high throughput and sensitive assay, it is ideal to use an in vitro device with a multitude of wells, containing cells, a small amount of assay material and automation. Classically, the determination of in vitro oral absorption characteristics is performed using a defined epithelium cell line and measuring the apparent transport rate of the drug across a monolayer of the cells. More recently it is possible to rank/order the passive transport rate of potential drug candidates using an artificial membrane barrier. The values generated from these in vitro experiments are valuable methods for screening the most likely successful drug candidates long before the oral absorption rate are validated by in vivo measurements. A typical experiment for determining the drug absorption characteristics of a known or unknown chemical compound is performed as follows. The multiwell device is seeded with epithelium cells on top of the filter in a defined nutrients medium. The same medium is also added to the single well feeding tray, located below and in fluid contact with the device containing the cells. The cells are allowed to proliferate and differentiate over a number of days. The nutrient medium is periodically replaced with fresh medium to replenish exhausted nutrients and remove waste and dead cells. At the end of a growing time, the cells and multiwell device are gently washed with an isotonic buffer to remove protein and residual nutrient medium. At this time, the multiwell filter plate is transferred to the multiwell receiver plate and the chemicals to be assayed are introduced to either the compartment above the cell layer or below the cells and filter support in the multiwell receiver tray. The opposing chamber is filled with drug free buffer and the multiwell device is incubated for some period of time, typically at 37 degrees Centigrade with shaking. If multiple time points are desired, samples are taken from either compartment and buffer then is added to make up for the liquid removed. Typically, if samples are taken from the lower compartment, the filter plate must first be removed, thus risking contamination of the material in the wells. The amount of drug/chemical that is transported across the cell barrier can be determined by a variety of analytical methods, but typically is determined using LC-MS/MS (Liquid Chromatography-Mass Spectrometry-Mass Spectrometry).

Accordingly, it would be desirable to provide a multiwell filter plate of a multiwell test apparatus which facilitates replenishing a nutrient medium in a feeding tray quickly and in a manner which preserves the integrity of the membranes and cells on the membrane. In addition, it would be desirable to provide such a multiwell filter plate which can be utilized in conjunction with a multiwell receiver plate subsequent for use in conjunction with the feeding tray.

SUMMARY OF THE INVENTION

This invention will be described herein with reference to the growing and use of cells on a permeable barrier, such as a porous membrane or a glass fibrous mat, positioned and secured to the bottom of each of a multiplicity of wells. However, it is to be understood that the present invention need not be used in conjunction with cells. Other representative uses include filtration, dialysis or the like.

The present invention provides a multiwell filter plate comprising a multiplicity of wells each including a membrane for retaining a sample, such as cells on the membrane for use in a multiwell test apparatus. The multiwell filter plate is first used in conjunction with a feeding tray in a step wherein cell growth is promoted and then is used in conjunction with a multiwell receiver plate wherein sample testing is effected. The feeding tray promotes quick replenishment of the nutrient medium while avoiding damage to membranes secured to a multiplicity of wells or damage to cells positioned on the membranes. The feeding tray can include a flat or inclined bottom surface. The bottom surface is preferably inclined so that the nutrient medium will flow to a low point of the inclined bottom surface as the nutrient medium is removed through one or more access holes of the multiwell filter plate from the bottom surface of the feeding tray, preferably at the low point of the inclined bottom surface.

The multiwell filter plate of this invention is provided with an input access hole or slot through which the nutrient medium is supplied to the feeding tray and is provided with a drainage access hole or slot through which the nutrient medium is removed from the feeding tray. The access holes permit insertion of a liquid handling device such as a syringe, cannula, pipette or the like therethrough, for introduction or drainage of the nutrient medium while avoiding the need for separating the multiwell filter plate from the feeding tray in order to replenish or supply nutrient medium to the feeding tray. Alternatively, the nutrient can be both removed and added through a single access hole at a low point of an inclined bottom support of a feeding tray. In a further alternative, the use of the filter plate having one or more openings providing access to the feeding tray may be used in conjunction with a flat bottomed feeding tray.

In another embodiment, the present invention provides a multiwell filter plate comprising a multiplicity of wells each including a membrane for retaining a sample, such as cells on the membrane for use in a multiwell test apparatus. The wells of the multiwell filter plate are shaped to form at least one shelf extending from a wall of the well and spaced apart from the membrane so that the shelf provides a support surface for an end of the liquid handling device such as a syringe, cannula, pipette or the like to prevent its contact with the permeable barrier, typically a membrane, and the growing cells. Additionally, the shelf serves as a deflector when media is injected into the well. The shelf allows the media to be added without disturbing the growing cells.

The multiwell filter plate of this invention is used in a second step in conjunction with a multiwell receiver plate, the wells of which house a liquid that interacts with the membrane or cells within the wells of the multiwell filter tray. An access hole is positioned adjacent each well of the multiwell filter tray to provide direct access to the wells of the multiwell receiver plate positioned below the multiwell filter plate.

DESCRIPTION OF SPECIFIC EMBODIMENTS

While the present invention is described with reference to effecting cell growth in a multiplicity of wells, it is to be understood that the present invention is applicable to manipulations involving access areas for introducing or removing a liquid to effect the desired processing, for example dialysis or diffusional separation while avoiding movement of membranes in the wells.

Figure 1A:
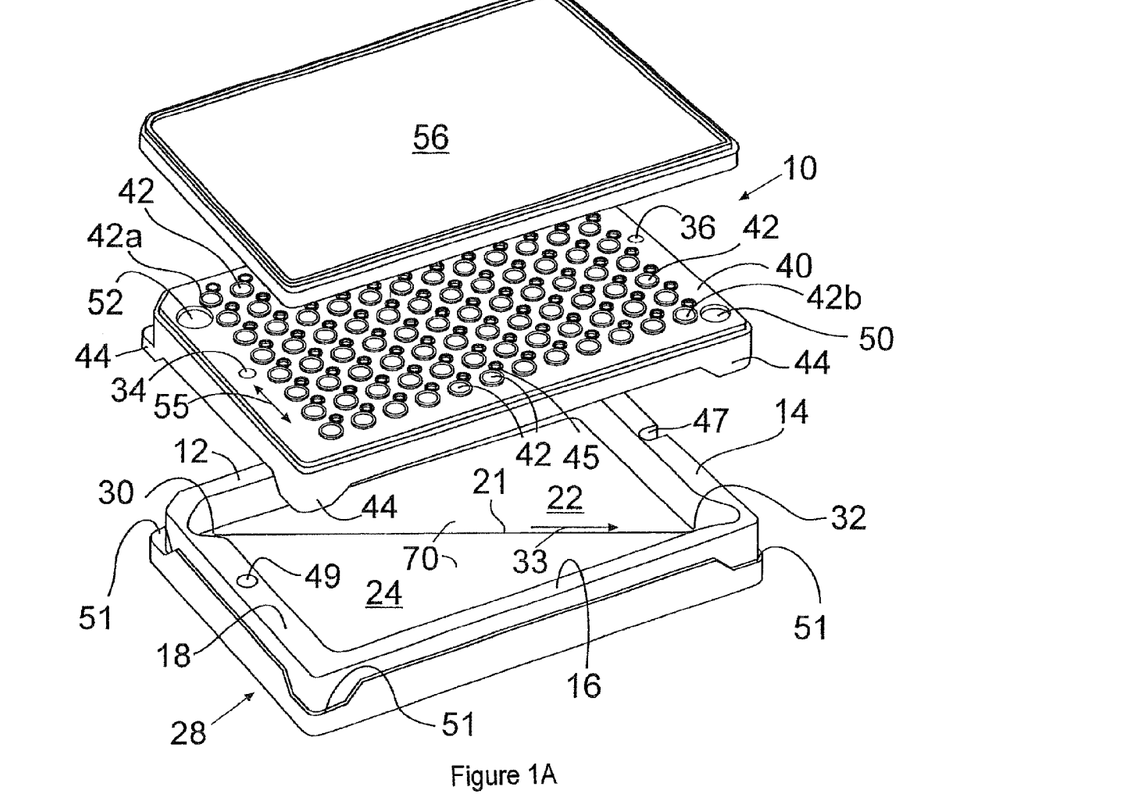
FIG. 1A is a top exploded view of a multiwell test apparatus utilizing the filter plate of this invention.
Figure 1B:
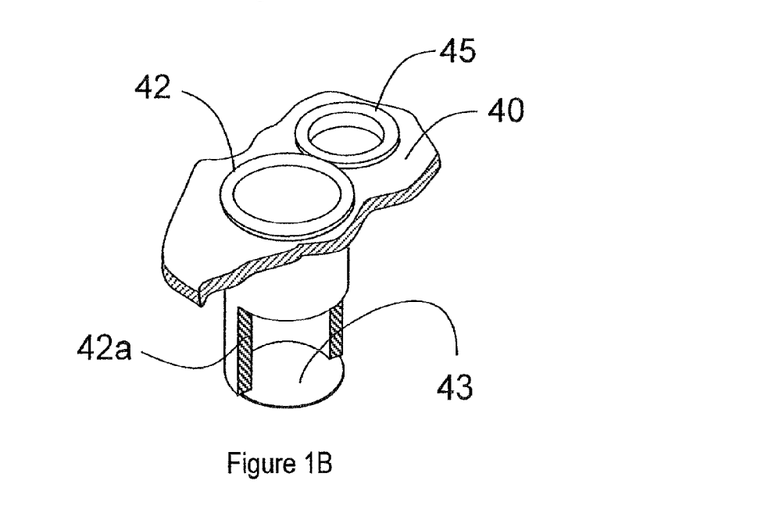
FIG. 1B is a partial cross-sectional view of the wells of the multiwell filter plate of FIG. 1A.

Referring to FIGS. 1A and 1B, the multiwell filter plate 10 of this invention comprises a plate 40 including a plurality of wells 42, each of which is paired with an access hole 45. As shown in FIG. 1B, each well 42 comprises a tubular member 42a having a lower opening to which is secured a membrane 43 such as a microporous membrane. While the member is preferably tubular in shape, other shapes can also be used such as triangular, rectangular, square or hexagonal. The multiwell filter plate 10 includes an access hole 50 which provides access to a drainage area 32 of feeding tray 28 from which liquid can be supplied to and/or drained from feeding tray 28.

Preferably, the nutrient medium can be replenished through a separate access hole 52 in filter plate 10. Liquid nutrient composition can be drained from feeding tray 28 through access hole 50. Replenishment and drainage can be effected with a conventional syringe apparatus. As shown in this embodiment, the feeding tray has an inclined bottom surface such that the drainage area 32 is positioned at the lowest point of the bottom surface 70 of feeding tray 28 and complete drainage can be easily effected. Drainage and replenishment can be effected simultaneously without the need to move multiwell filter plate 10 relative to feeding tray 28. Removable lid 56 is utilized to isolate the wells 42 from the atmosphere surrounding the multiwell filter plate 10 thereby to reduce evaporation of the nutrient medium and contamination of the well. It is evident that the nutrient medium can be added and removed through a single access hole at a low point of the inclined bottom surface. Separate areas for addition and removal effects a flushing action to improve the removal of nutrient medium to and from the feeding tray 28 of spent nutrient medium.

In an alternative arrangement (not shown) the feeding plate may have a flat bottom. Al other features described and shown in relation to FIGS. 1A and 1B remain the same.

In the embodiment shown in FIGS. 2A and 2B, multiwell filter plate 10 is provided with posts 34 and 36 which fit respectively in holes 46 and 48 of multiwell receiver plate 29 when multiwell receiver plate 29 is positioned below multiwell filter plate 10,. Alternatively posts 34 and 36 can be positioned within holes 49 and 47 of feeding tray 28 when feeding tray 28 is positioned below multiwell filter plate 10 as shown in FIG. 1A. Posts 34 and 36 are positioned asymmetrically from each other in the direction of arrow 55 (FIG. 1A) so that well 42a is always in the upper left hand position while well 42b is always in the lower right hand position shown in FIG. 1A. By so positioning wells 42a and 42b, all the wells 42 in filter plate 10 can be identified by their position while preventing movement of multiwell filter plate 10 so that capillary pumping of liquid within wells 42 is prevented.

Figure 2A:
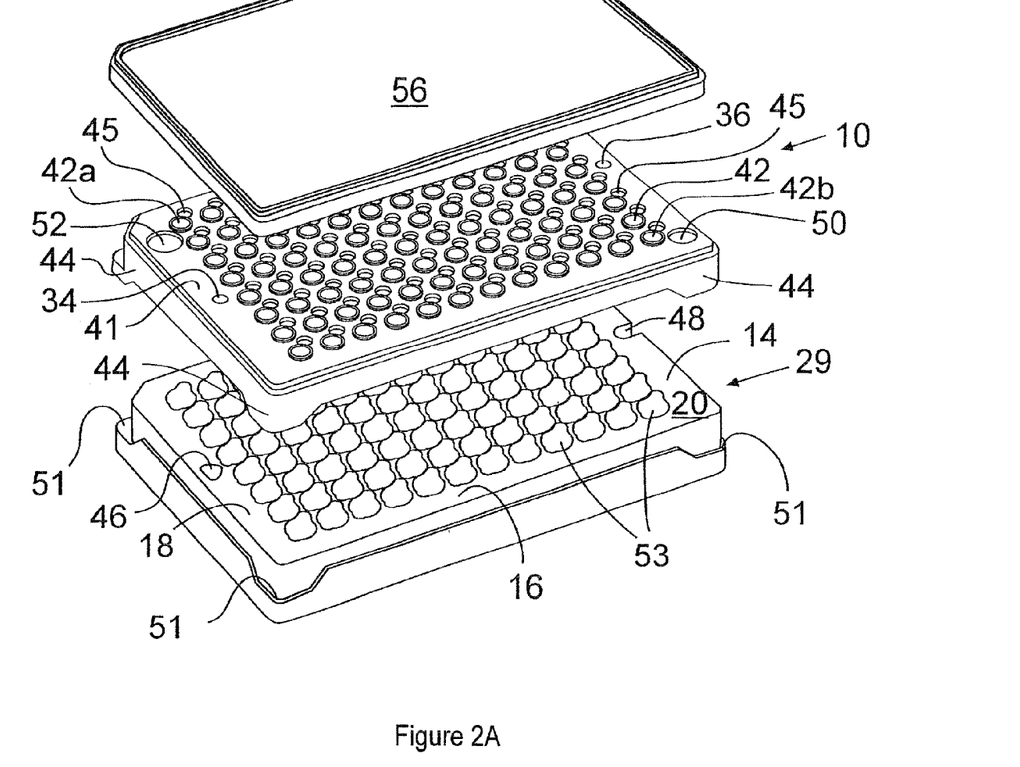
FIG. 2A is a top partial view of the multiwell filter plate of this invention positioned above a multiwell receiver plate.
Figure 2B:
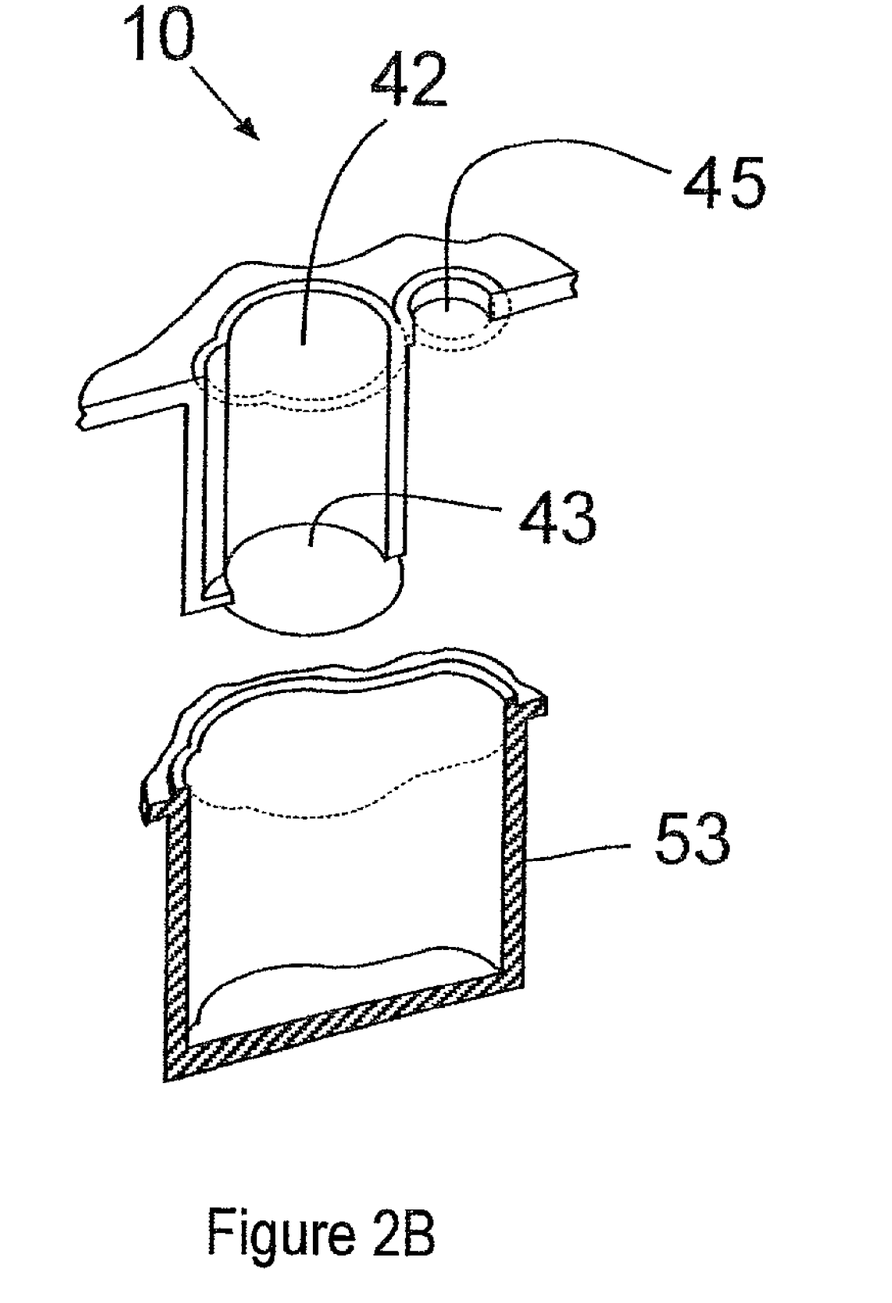
FIG. 2B is a partial cross-sectional view of the multiwell filter plate and multiwell receiver plate.

The use of filter plate 10 is also exemplified with reference to FIGS. 2A and 2B. As shown in FIGS. 2A and 2B, the multiwell filter plate 10 is positioned above multiwell receiver plate 29 which includes a multiplicity of wells 53, such as 96 wells. In use, the multiwell receiver plate 29 is positioned such that each membrane 43 (FIG. 2B) of the wells 42 extends into only one well 53. Each of the wells 42 has associated therewith an access hole 45 which permits access to a well 53 of a multiwell receiver plate 29 utilized during a sample assay step. The wells 53 are shaped to accommodate wells 42 and to permit access thereto through holes 45. The multiwell filter plate 10 can be provided with four legs 44 which fit into recesses 51 of multiwell receiver plate 29 thereby to provide mechanical stability of multiwell filter plate 10. The legs also serve to position the membranes 43 to avoid contact with the bottom surfaces of the wells 53 thereby to prevent contact of the bottom surfaces of the wells 53 with the membranes 43.

Figure 3:
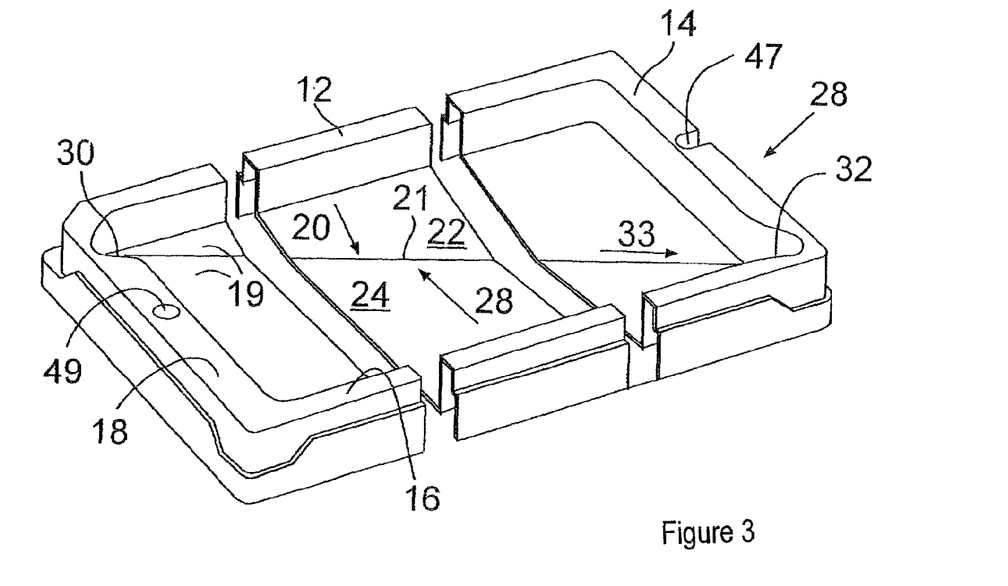
FIG. 3 is a top view of a feeding tray which can be utilized with the multiwell filter plate of this invention.

Referring to FIG. 3, the feeding tray 28 utilized with the multiwell filter plate of this invention includes walls 12, 14, 16 and 18 and bottom surface 19 to house a nutrient medium. The bottom surface includes two surface subsections 22 and 24 separated by drain path 21. The surface subsections 22 and 24 are inclined downwardly from walls 12 and 16 in the direction exemplified by arrows 20 and 28 toward drain path 21. Drain path 21 provides fluid flow from liquid introduction area 30 on the bottom surface to liquid drain area 32 as exemplified by arrow 33.

An alternative embodiment of the design described above is shown in FIG. 4. In this embodiment, each well 100 of a filter plate 101 has an associated access hole 102, a permeable barrier layer 104 formed at the lower opening 106 of each well 102, a recess 108 and a shelf 110 formed adjacent the lower opening 106 and the lower portion of the recess 108. As shown each well is able to fit within a corresponding well 112 of a multiwell receiving plate 114.

Figure 4:
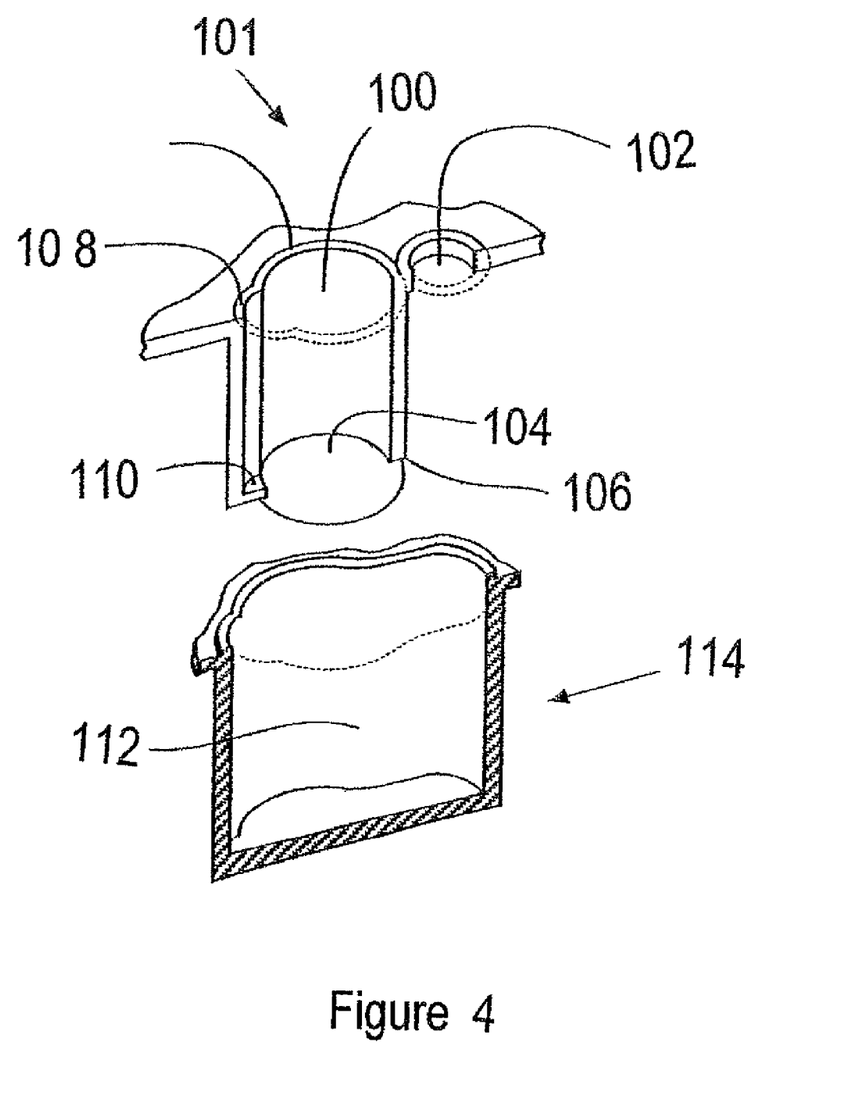
FIG. 4 is a partial cross-sectional view of the multiwell filter plate and multiwell receiver plate.
Figure 5:
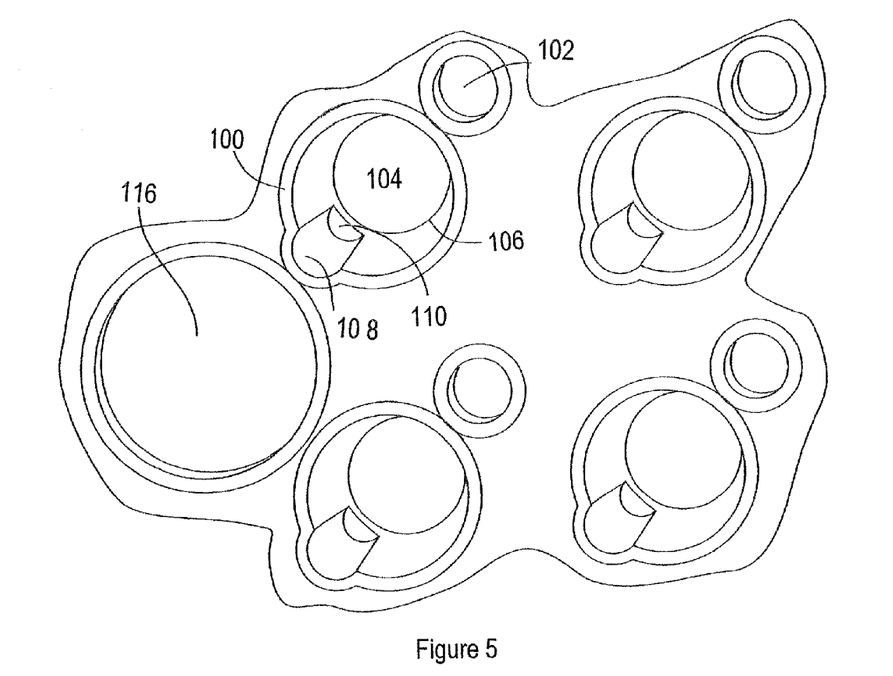
FIG. 5 is a top view of a multiwell filter plate of this invention.

FIG. 5 shows a top down perspective view of the device described in FIG. 4 along with access hole 116 which corresponds to the access hole 52 of FIG. 1A.

Figure 6A:
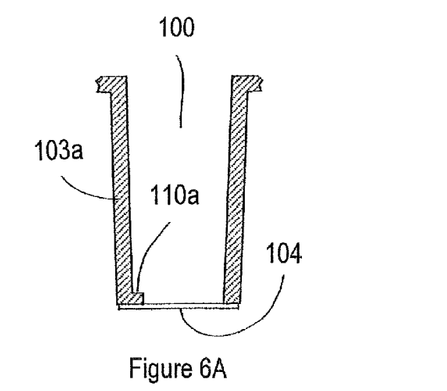
FIGS. 6A and B are a partial cross-sectional view of a well of the multiwell filter plate of the present invention.

Referring to FIG. 6A, the shelf 110a is formed by conventional molding wherein the shelf 110a extends from the well wall 103a.

Figure 6B:
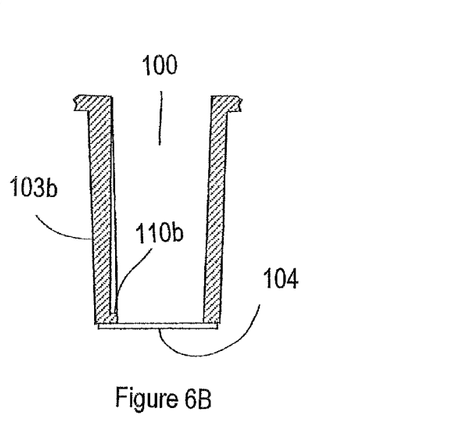

Referring to FIG. 6B, the shelf 110b is formed by conventional molding wherein a portion of well wall 103b is recessed.

Figure 7:
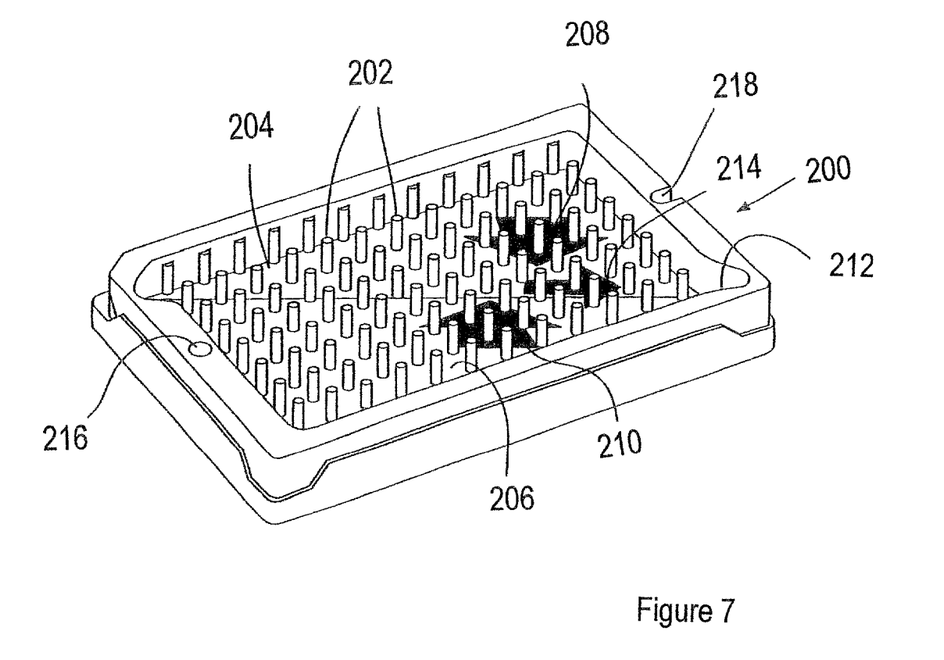
FIG. 7 is a top view of a single well receiver plate of this invention.

Referring to FIG. 7, an alternative feeding tray 200 utilized with the multiwell filter plate of this invention is illustrated. This embodiment is provided with protrusions extending from the inner and supporting surface of the feeding tray a distance which permits their contact with the membranes of the wells of the multiwell filter plate. As shown, the protrusions are posts 202 extend from surfaces 204 and 206 to a position where they can contact the membrane 43 of wells 42 of the embodiment of FIG. 1 or the membrane 104 of the well 100 of the embodiment of FIG. 4. The purpose of this contact is to effect drainage of excess liquid from the bottom surface of the membrane 43 or 104 to the posts 202 and into the feeding tray 200. This practice is commonly called "touch-off" in the field of pipetting and means to remove residual liquids/sample adhering to pipette tips. The shape of the protrusions may be varied so long as they provide the same function. Typical shapes include conical, pyramidal, rectangular and dimpled. A post 202 is positioned adjacent each well 42 or 100. As shown, the feeding tray 200 also comprises inclined surfaces 204 and 206 which effect liquid flow in the directions of arrows 208 and 210 and in the direction of arrow 214 into the drainage area 212. However, a flat bottomed or other shaped feeding tray may equally be used if desired. Movement of a multiwell filter plate toward posts 202 can be effected by any conventional means.

Figure 8:
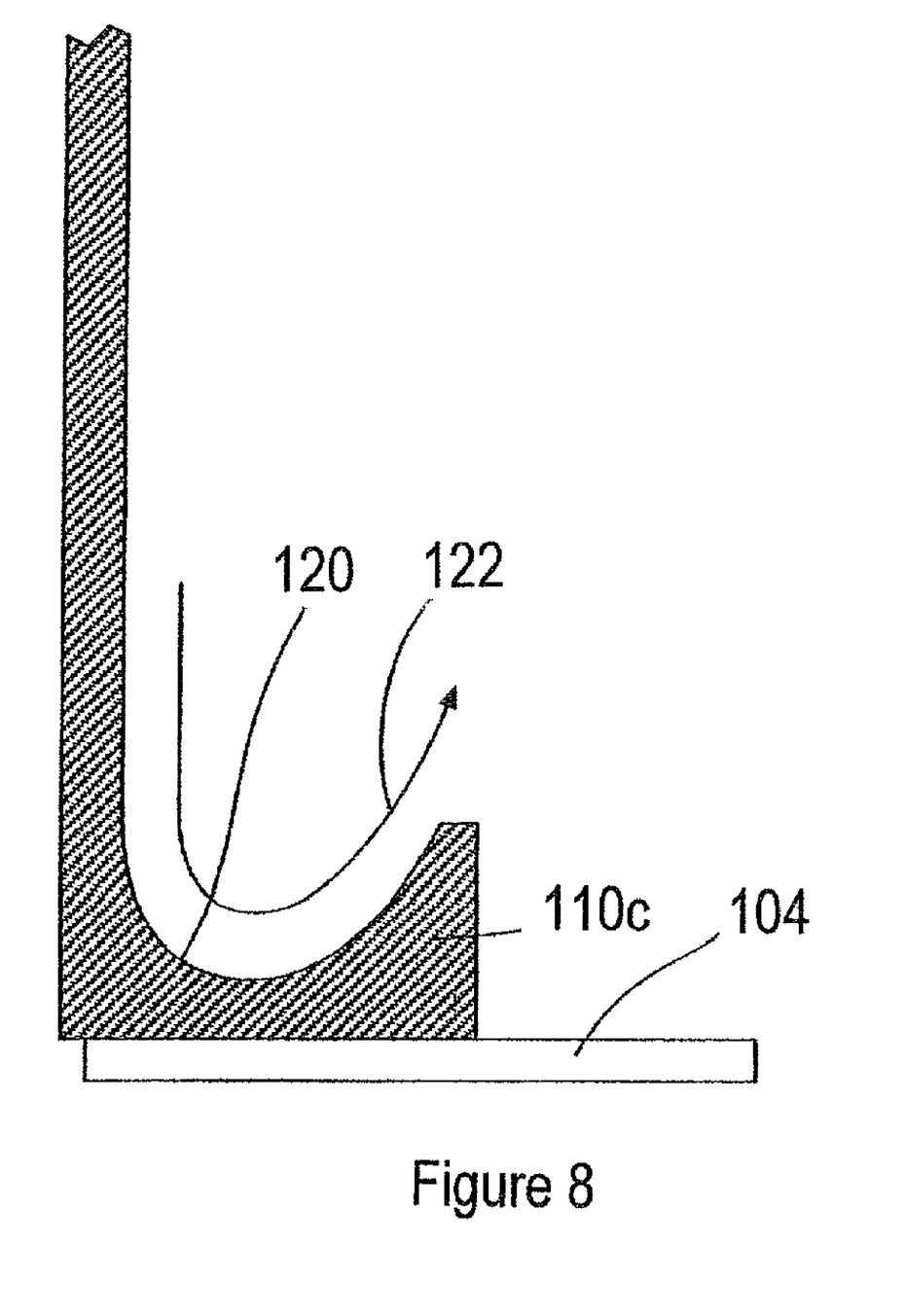
FIG. 8 is a partial cross-sectional view of a well of the multiwell filter plate of the present invention.

As shown in FIG. 8, the shelf 110c can include a concave surface 120 which serves to direct liquid from a syringe, cannula, pipette and the like in the direction shown by arrow 122. This serves to reduce the pressure of the liquid from the syringe on membrane 104 thereby preserving the integrity of the membrane 104 and preserving the integrity of a cell layer on membrane 104.

What we claim:

1. A multiwell filter plate which comprises, a multiplicity of wells extending from a plate, each of said wells comprising (a) a hollow member having two openings and extending from said plate and (b) a permeable barrier secured about said opening extending from the plate,
   a first access hole through said plate for passing liquid through said plate to effect contact of said liquid with all of said permeable barriers,
   a set of second access holes extending through the plate, each second access hole being positioned adjacent each one of said multiplicity of wells.

2. The multiwell filter plate of claim 1 further comprising a third access hole for passing liquid through said plate to remove liquid from contact with all of said barriers.

3. The filter plate of claim 1 further comprising a shelf extending inwardly from a wall of the hollow member adjacent the porous membrane secured about said opening and wherein said shelf is formed by a recess in said wall.

4. A multiwell test apparatus comprising the multiwell filter plate of claim 1 and a feeding tray supporting said filter tray, said feeding tray having an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface.

5. The multiwell test apparatus of claim 4 wherein said inclined support surface comprises two support surface subsections each inclined from said walls to a drainage path connected to both of said support surface subsections.

6. The multiwell test apparatus of any one of claims 4 or 5 which includes a multiplicity of protrusions extending from said support surface in a direction substantially the same as a direction said walls extend from said support surface, said protrusions having a length which permits said walls to support said multiwell filter plate and to permit contact of said protrusions with each membrane of a well of said filter plate when said filter plate is removed from support by said feed tray.

7. The multiwell test apparatus of claim 6 wherein said protrusions are selected from the group consisting of posts, pyramids, rectangles, dimples and cones.

8. A multiwell filter plate which comprises a multiplicity of wells extending from a plate, each of said wells comprising (a) a hollow member having two openings and extending from said plate and (b) a permeable barrier secured about said opening extending from the plate;
   a first access hole through said plate for passing liquid through said plate to effect contact of said liquid with all of said permeable barriers;
   a feeding tray supporting said filter tray, said feeding tray having an inclined support surface having a drainage area from which liquid can be removed and an introduction area into which liquid can be supplied, said inclined support surface being inclined in a configuration to effect drainage of liquid from said introduction area to said drainage area, and walls surrounding said inclined surface to enclose said inclined surface and wherein said inclined support surface comprises two support surface subsections each inclined from said walls to a drainage path connected to both of said support surface subsections.

9. A device for effecting cell growth comprising a filter plate having a plurality of wells, a first access port paired with each well, each well having a lower opening to which is secured a membrane; a feeding tray comprising a flat bottom and four sides into which the wells of the filter plate extend and at least one second access hole in the filter plate for passing liquid through the filter plate into the feeding tray without the need to move the filter plate relative to the feeding tray.

10. A device for effecting cell growth comprising a filter plate having a plurality of wells, a first access port paired with each well, each well having a lower opening to which is secured a membrane, a recess formed in a sidewall of each well and extending to the lower opening and a shelf formed adjacent the lower opening and at a lower portion of the recess; a feeding tray comprising a flat bottom and four sides into which the wells of the filter plate extend and at least one second access hole in the filter plate for passing liquid through the filter plate into the feeding tray without the need to move the filter plate relative to the feeding tray.

11. A device for effecting cell growth comprising a filter plate having a plurality of wells, a first access port paired with each well, each well having a lower opening to which is secured a membrane and a plurality of legs extending from a surface of the filter plate at a distance longer than the length of said wells; a feeding tray comprising a flat bottom and four sides into which the wells of the filter plate extend and at least one second access hole in the filter plate for passing liquid through the filter plate into the feeding tray without the need to move the filter plate relative to the feeding tray.

12. A multiwell filter plate which comprises, a multiplicity of wells extending from a plate, each of said wells comprising (a) a hollow member having two openings and extending from said plate and (b) a permeable barrier secured about said opening extending from the plate, a first access hole through said plate for passing liquid through said plate to effect contact of said liquid with all of said permeable barriers, a set of second access holes extending through the plate, each second access hole being positioned adjacent each one of said multiplicity of wells, and a shelf extending inwardly from a wall of the hollow member adjacent the porous membrane secured about said opening, said shelf having a top concave surface.

13. The plate of claim 12 wherein said shelf is formed by a recess in said wall.

14. A multiwell filter plate which comprises, a multiplicity of wells extending from a plate, each of said wells comprising (a) a hollow member having two openings and extending from said plate and (b) a permeable barrier secured about said opening extending from the plate, a first access hole through said plate for passing liquid through said plate to effect contact of said liquid with all of said permeable barriers, a set of second access holes extending through the plate, each second access hole being positioned adjacent each one of said multiplicity of wells, and a third access hole through said plate for passing liquid through said plate to remove the liquid from contact with all of said barriers.

* * * * *